(12) United States Patent
Hunt et al.

(10) Patent No.: US 6,780,154 B2
(45) Date of Patent: Aug. 24, 2004

(54) SEGMENTED HANDHELD MEDICAL ULTRASOUND SYSTEM AND METHOD

(75) Inventors: Robert P. Hunt, Maple Valley, WA (US); John C. Lazenby, Fall City, WA (US); Robert N. Phelps, Sammamish, WA (US); David A. Petersen, Fall City, WA (US); Stephen B. Hooper, Seattle, WA (US); Heike Seck, Issaquah, WA (US); Jerry D. Hopple, Woodinville, WA (US); Bhavani Duggirala, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 36 days.

(21) Appl. No.: 10/341,816

(22) Filed: Jan. 14, 2003

(65) Prior Publication Data

US 2003/0139664 A1 Jul. 24, 2003

Related U.S. Application Data

(60) Provisional application No. 60/349,949, filed on Jan. 17, 2002.

(51) Int. Cl.$^7$ ................................................. A61B 8/06
(52) U.S. Cl. ...................................................... 600/446
(58) Field of Search ................................. 600/437, 438, 600/440, 441, 442, 443, 446, 447, 448, 449, 459, 461–472; 73/595–633; 367/7, 11, 130, 138; 128/916

(56) References Cited

U.S. PATENT DOCUMENTS

| | | |
|---|---|---|
| 5,548,564 A | 8/1996 | Smith |
| 5,579,768 A | 12/1996 | Klesenski |
| 5,590,658 A | 1/1997 | Chiang et al. |
| 5,690,114 A | 11/1997 | Chiang et al. |
| 5,722,412 A | 3/1998 | Pflugrath et al. |
| 5,817,024 A | 10/1998 | Ogle et al. |
| 5,839,442 A | 11/1998 | Chiang et al. |
| 5,945,770 A | 8/1999 | Hanafy |
| 5,957,846 A | 9/1999 | Chiang et al. |
| 5,957,851 A | 9/1999 | Hossack |
| 5,964,709 A | 10/1999 | Chiang et al. |
| 6,106,472 A | 8/2000 | Chiang et al. |
| 6,113,547 A | 9/2000 | Catallo et al. |
| 6,117,085 A | 9/2000 | Picatti et al. |
| 6,121,718 A | 9/2000 | Mohr, III |
| 6,135,961 A | 10/2000 | Pflugrath et al. |
| 6,142,946 A | 11/2000 | Hwang et al. |
| 6,251,073 B1 | 6/2001 | Imran et al. |
| 6,383,139 B1 | 5/2002 | Hwang et al. |
| 6,398,733 B1 | 6/2002 | Simopoulos et al. |
| 6,416,475 B1 | 7/2002 | Hwang et al. |
| 6,471,651 B1 | 10/2002 | Hwang et al. |

OTHER PUBLICATIONS

"Head–up Display Can Be Built Into Eyeglasses," by David Lieberman, EE Times, The Industry Source For Engineers & Technical Managers Worldwide; eetimes.com/story/OEG19990420S0009; Apr. 20, 1999.

"NCO Helps Create New Ultrasound Technology," by 2$^{nd}$ Lt. Nathan Broshear 82$^{nd}$ Training Wing Public Affairs; Public Affairs (AETC News Service); Jul. 10, 2002.

MicroOptical—Making Portable Practical; www.microopticalcorp.com/applications.html; date unknown (printed Nov. 11, 2002.

*Primary Examiner*—Ali Imam

(57) ABSTRACT

A segmented ultrasound system is provided. Ultrasound data, such as image data in a video format, is wirelessly transmitted to a multi-use display device from a handheld ultrasound device. Any of various multi-use display devices may be used, such as personal digital assistants (PDA), tablet computers, lap top computers, or personal computers.

30 Claims, 3 Drawing Sheets

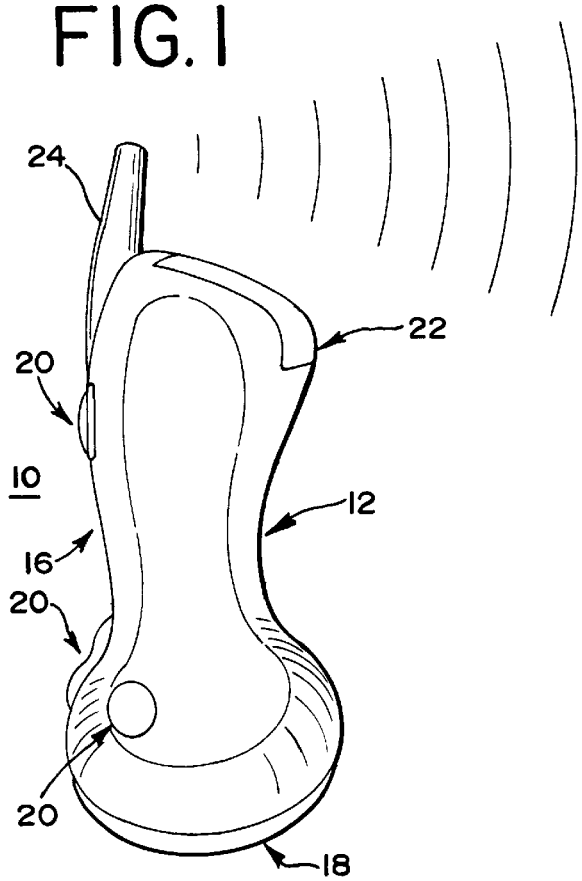
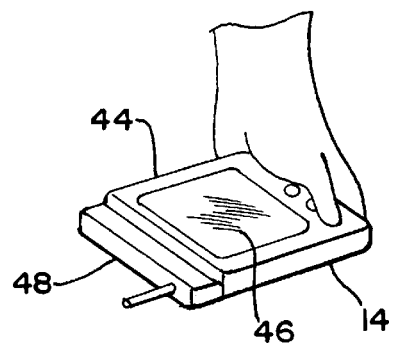
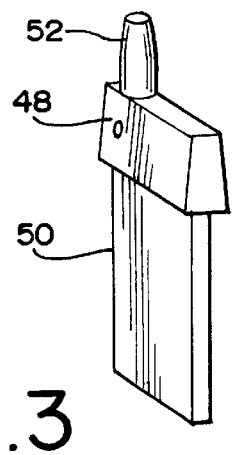
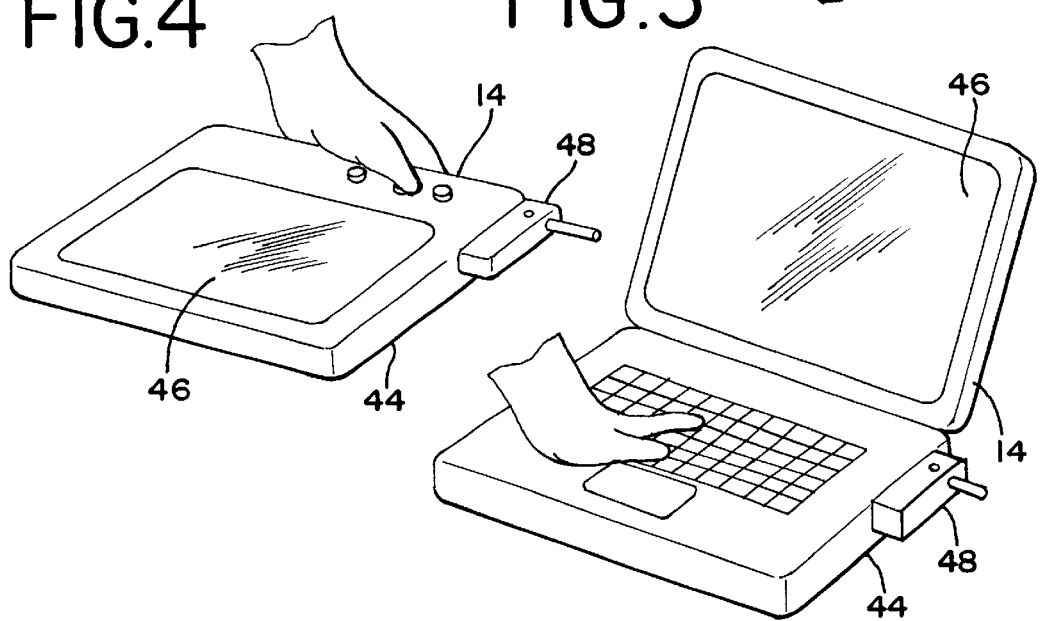

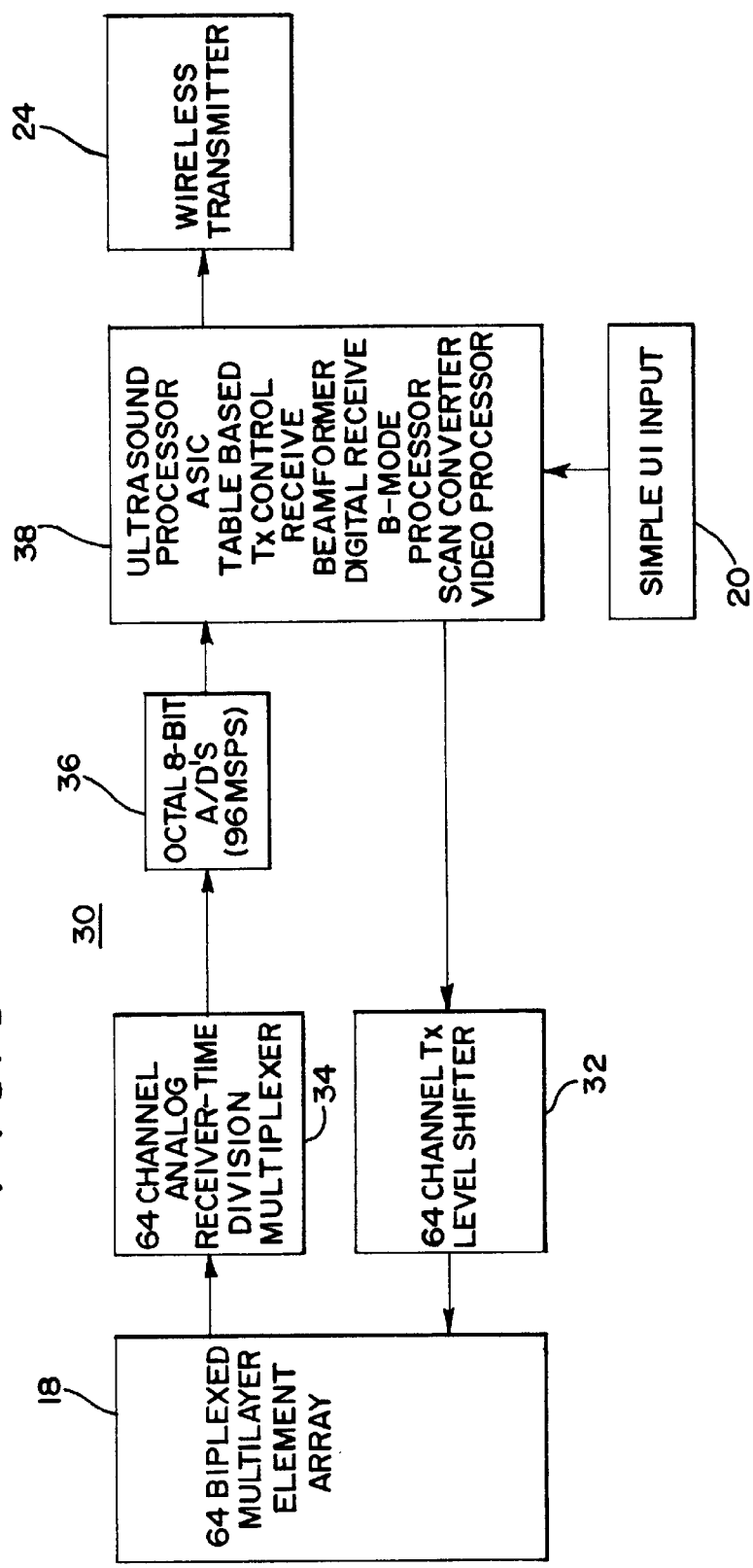

SEGMENTED HANDHELD MEDICAL ULTRASOUND SYSTEM AND METHOD

RELATED APPLICATIONS

This application claims the benefit of the filing date pursuant to 35 U.S.C. §119(e) of Provisional Application Serial No. 60/349,949 (Medical Hand-held Device), filed Jan. 17, 2002, the disclosure of which is incorporated herein by reference.

BACKGROUND

The present invention relates to portable diagnostic ultrasound systems. In particular, a segmented hand-held ultrasound system is provided.

Conventional ultrasound imaging systems typically include a hand-held transducer probe coupled by a cable to a large processing and display workstation. The transducer probe includes an array of ultrasonic elements which transmit and receive ultrasonic energy for imaging a patient. The received ultrasonic energy is converted to electric signals by the transducer and passed to the workstation. The workstation detects, filters and otherwise processes the information to generate a two- or three-dimensional representation of the scanned region. Limited mobility is provided by such systems. Typically, the ultrasound system is maintained in a specific location and patients are brought to the ultrasound system, but the system may be used on a wheeled cart.

A more portable ultrasound system is disclosed in U.S. Pat. No. 6,312,381, the disclosure of which is incorporated herein by reference. The system shown in FIG. 11 of the '381 patent is designed to be carried by a single person, such as weighing less than 30 pounds. The system includes a large screen and a keyboard. The system is carried as a briefcase or package.

Additional portability is provided by one or more of the systems disclosed in U.S. Pat. Nos. 5,957,846, 6,251,073, 5,817,024 and 6,383,139, the disclosures of which are incorporated herein by reference. Different amounts of portability are provided. For example, one system includes a hand-held scan head coupled by a cable to a portable data processor and display unit, such as a laptop computer. Other systems include separate hand-held components including a small display screen and transducer components.

BRIEF SUMMARY

The present invention is defined by the following claims, and nothing in this section should be taken as a limitation on those claims. By way of introduction, the preferred embodiments described below include a segmented handheld ultrasound device. Ultrasound data, such as image data in a video format, is wirelessly transmitted to a multi-use display device. Any of various multi-use display devices may be used, such as personal digital assistants (PDA), tablet computers, lap top computers, or personal computers.

In one aspect, a handheld system for medical diagnostic ultrasound imaging includes a transducer and an ultrasound processor in communication with the transducer. A housing encloses the ultrasound processor. The housing is adapted to be handheld. A multi-use display device is used separate from the housing and receives data wirelessly from the ultrasound processor. The multi-use display device is operable for a use other than associated with ultrasound and operable to display an ultrasound image responsive to the ultrasound processor.

In a second aspect, a method for medical diagnostic ultrasound imaging with a handheld system is provided. A transducer is held adjacent a patient. Ultrasound data representing the patient is generated. The ultrasound data is wirelessly transmitted from a portable housing to a multi-use display device. The multi-use display device is operable for a use other than associated with ultrasound. An ultrasound image is displayed on the multi-use display device.

In a third aspect, a handheld system for medical diagnostic ultrasound imaging includes a handheld image processing ultrasound device free of a display. A transmitter is housed with the handheld image processing ultrasound device. The transmitter is operable to wirelessly transmit ultrasound image data in a video format.

In a fourth aspect, a method for medical diagnostic ultrasound imaging with a handheld system is provided. Ultrasound image data is generated in a video format with a handheld ultrasound device. The ultrasound image data is wirelessly transmitted in the video format from the handheld ultrasound device.

Further aspects and advantages of the invention are discussed below in conjunction with the preferred embodiments. Any later added claims based on the matter below are intended to be within the scope of the invention.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a front view of a handheld ultrasound device of one embodiment.

FIG. 2A is a perspective view of one embodiment of a multi-use display device.

FIG. 2B is a perspective view of one embodiment of a card for use with the multi-use display device of FIG. 2A.

FIGS. 3 and 4 are perspective views of other embodiments of multi-use display devices.

FIG. 5 is a block diagram of one embodiment of the circuit of the handheld ultrasound device of FIG. 1.

DETAILED DESCRIPTION OF THE PREFERRED EMBODIMENTS

Figure 6:
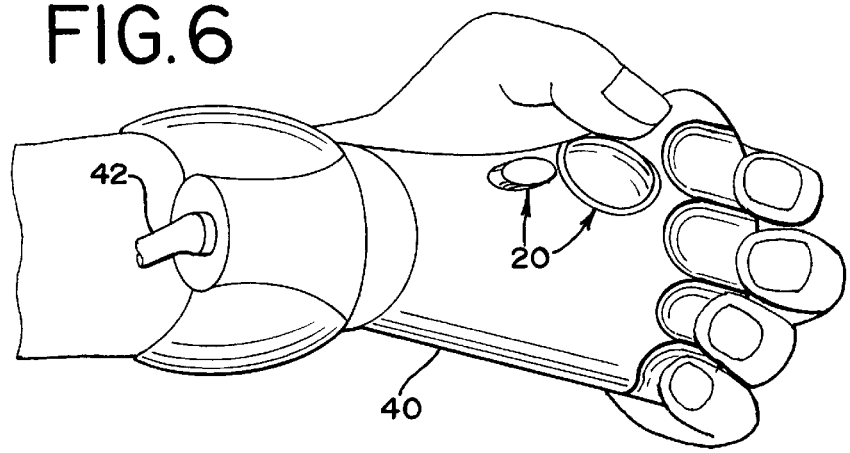
FIGS. 6 and 7 are two embodiments of user controls for handheld ultrasound devices.

Many medical care providers have access to consumer based information display devices and, in the future, more common display devices may be carried by medical personnel. For example, off-the-shelf personal digital assistants (PDA), tablet computers, notebook or lap top computers, or other multi-use display devices are common. By obtaining ultrasound data and outputting the data in a video format or other format usable by these common display devices, easy and convenient ultrasound examination may be possible. By providing a dedicated ultrasound device free of a display to obtain and transmit standard video data, the common display device uses a standard interface for receiving the video data. Software on the common display device allows formatting of the video ultrasound data. Since a multi-use display is used, information associated with the other uses, such as patient data, treatment data, time, or other types of medical images may be displayed with static or real-time ultrasound images.

FIG. 1 shows part of a handheld system 10 for medical diagnostic ultrasound imaging. The system 10 includes a handheld image processing ultrasound device 12 and a multi-use display device 14 (see FIGS. 2A, 3 and 4). The handheld image processing ultrasound device 12 obtains ultrasound data and formats the ultrasound data for transmission to the multi-use display device 14. The handheld image processing ultrasound device 12 is free of a display, but a display (e.g. a flip out screen, LCD or miniature display) may be provided on the ultrasound device 12.

The handheld image processing ultrasound device 12 comprises a housing 16, a transducer 18, user controls 20, a battery 22 and a transmitter 24. Additional, different or fewer components may be provided, such as the ultrasound device 12 without user controls 20 and/or without the transducer 18 in the housing 16.

The housing 16 is adapted to be portable or handheld, such as being less than 8 inches in any dimension and/or having an ergonomic shape for holding in a users hand. The housing 16 comprises plastic, rubber, metal, other materials now known or later developed, or combinations thereof. In one embodiment shown in FIG. 1, the housing 16 is shaped for ergonomic use or holding by the user by having a generally round or curved circumference acting as a grip. Other shapes adapted to be held by a user's hand may be used, such as a housing with a handle. In other embodiments, different shapes are used, such as a more angular, box or irregular shape with or without belt or shoulder strap attachments. For portability, the housing 16 is less than twelve, less than eight or less than six inches in any dimension. For example, the housing 16 is about six inches long and has a generally round circumference sized to fit within a user's hand.

The handheld image processing ultrasound device 12 includes ultrasound circuitry within the housing 16. FIG. 5 shows one embodiment of the ultrasound circuitry 30. The ultrasound circuitry 30 includes the transducer 18, a level shifter or transmit beamformer 32, a receiver 34, analog-to-digital converters 36, an ultrasound processor 38, the user controls 20 and a wireless transmitter 24. Additional, different or fewer components may be used, such as providing the transmit and/or receive beamformers 32, 34 in a different housing or having multiple processors, analog circuits or digital circuits for any of the transmit beamformer 32, the receiver 34, the ultrasound processor 38 or the wireless transmitter 40. In one embodiment, the ultrasound circuits 30 and/or the housing 16 as described in U.S. application Ser. No. 10/341,871 filed on the same day as this application as IMMERSIVE PORTABLE ULTRASOUND SYSTEM AND METHOD), the disclosure of which is incorporated herein by reference, are used.

The transducer 18 comprises an array of elements for transducing between acoustical and electrical energies, such as a one-dimensional, 1.5D, two-dimensional or single element transducer. Any of a phased array, linear array, curved array or other arrays may be used. An acoustic window is positioned on the housing 16 adjacent to the transducer 18. In one embodiment, the transducer 18 is sized to be small for portability, such as using more closely-spaced elements adapted for higher ultrasound frequencies or using fewer elements within the array (e.g. 64 elements as opposed to 128 elements). In alternative embodiments, the transducer 18 is larger. Any of various transducers 18 now known or later developed may be used, such as a cardiac transducer.

To keep the power supply as simple and as small as possible, the number of different power forms or voltages required within the handheld image processing ultrasound device 12 is reduced or kept at a minimum, such as one voltage provided for transmit and receive analog functions and a second voltage provided for analog to digital conversion and digital signal processing. To avoid a high voltage supply requirements, a step-up transformer and conventional PZT elements are used a multilayer PZT are used, a CMUT is used or combinations thereof. Any of various multilayer transducer structures may be used, such as disclosed in U.S. Pat. Nos. 5,548,564, 5,957,851, 5,945,770, 6,121,718, and 6,429,574, the disclosures of which are incorporated herein by reference. Since the voltages of each layer effectively sum, a lesser peak voltage drives the transducer 18 to create a similar peak acoustic pressure as a single layer element. For example, a total voltage differential of 20 volts is driven by application of 10 volt peak to each of two layers. Other peak voltages for each layer or as a sum of the layers may be used.

In order to further reduce power consumption, a plane wave or widely dispersed transmit beam is used with reception along multiple lines, reducing the number of transmit events. In one embodiment, all of or a subset of the elements of the transducer 18 are used. Alternatively, one or more dedicated transmit elements are positioned adjacent to dedicated receive elements. By positioning transmit elements on each side of a receive array, the transmitters are capable of generating ultrasound pressure appearing to emanate from a single point in space.

In one embodiment, the transducer 18 is within the housing 16 along with all or at least other portions of the ultrasound circuitry 30. In an alternative embodiment, a probe housing separate from the housing 16 for the ultrasound processor 38 is used. The transducer 18 is within the probe housing. The transducer 18 electrically and physically connects with the housing 16 through one or more cords. The cords comprise wires, coaxial cables, such as miniaturized coaxial cables, or other conductors wrapped in a protective sheath. Separate electrical connections may be provided for each element of the transducer 18 to the remaining ultrasound circuitry 30, but multiplexing may be used to minimize the number of cables. In other embodiments, additional ultrasound circuitry, such as the ultrasound circuitry 20 for detecting and scan converting are provided in a separate probe housing with the transducer 18.

As an alternative to connection with a cable for a separate probe housing, a radio frequency, infrared or other wireless connection connects the transducer 18 in a separate housing to the ultrasound processor in the housing 16. The probe housing includes a transmitter, a receiver and/or a transceiver. Data from one or more elements of the transducer 18 is multiplexed using any of various communications formats, such as time or frequency multiplexing schemes now known or later developed or an ultra wide band frequency format. The transmission is optimized for any of various distances, such as around two meters of range. Multiple directional infrared receivers, directional infrared transmitters and receivers, infrared or radio frequency control or feedback for control of automatic selection of the transmit frequency or receive antennas may be used to reduce the transmit power required. Analog or digital radio frequency transmissions may be used, such as a digital communication link with 0.1 to 2 megabits per second in an uncompressed or compressed format in a low power transmission. A battery or other power sources in the probe housing of the transducer 18 powers the electronics.

In one embodiment, the transducer 18 is releasably connectable with the housing 16 and the ultrasound circuitry 30.

For example, an electrical and physical connector is provided between the housing 16 and the transducer 18. The releasable connection allows for different transducers 18 to be connected with the housing 16. In alternative embodiments, the connection between the transducer 18 and the housing 16 is set or otherwise permanent.

With a separate probe housing or to reduce the number of analog-to-digital converters in an integrated housing 16, a multiplexer connects between the transducer 18 and the ultrasound processor 38. The transducer 18 may be free of further electronics or include additional electronics, such as preamplifiers, transmit and receive switches and/or portions of transmit and receive beam forming circuitry. For example, the transducer 18 includes time division multiplexing circuitry, such as disclosed in U.S. application Ser. No. 10/184,461 filed Jun. 27, 2002, the disclosure of which is incorporated herein by reference. A multiplexer, amplifiers and optional time gain controls are provided for multiplexing receive channels onto a single or fewer number of cables or signal lines than elements within the transducer 18. The multiplexer is provided in the receiver 34 in other embodiments.

The transmit beamformer 32 comprises one or more transmit pulsers, waveform generators, control circuits, switches, delays, timers, amplifiers, digital-to-analog converters or other now known or later developed analog or digital beamforming circuitry. In one embodiment, the transmit beamformer 32 comprises an analog application specific integrated circuit (ASIC) operating as a level shifter to drive a plurality of multilayer elements of the transducer 18. For example, the ASIC includes FET devices with very low or ultra low resistance (e.g., 20 milliohms) for running on a 5 volt power supply in response to unipolar waveform signals. In alternative embodiments, a split power supply with positive and negative voltages may achieve higher acoustic power and wider received dynamic range using bi-polar waveform signals. For each of 64 or other number of channels, two transistors drive a layer of an element during a transmit cycle and a transmit and receive switch is formed by two other transistors for isolating the receive circuitry. Transmit and receive switches may be avoided where a bi-plexed multilayer element transducer 18 is used. In another embodiment, the ASIC comprises a level shifter or amplifiers for driving the transducer 18 with beamformed signals provided to the ASIC (i.e. the transmit beamforming is performed, in part, in the ultrasound processor 38).

The receiver 34 comprises one or more amplifiers, preamplifiers, time gain control amplifiers, filters, summers, delays, buffers, multiplexers or other now known or later developed receiver circuitry. In one embodiment, the receiver 34 comprises an analog ASIC for preamplification, time gain control, and multiplexing. The receiver ASIC is separate from or included with the transmit beamformer ASIC. The receiver ASIC processes two or more, such as sixteen, parallel beams in response to one transmission, reducing the number of transmissions to scan a region. In one embodiment, the receiver 34 includes multiplexers, such as a eight 8-to-1 multiplexers, to reduce the number of analog-to-digital converters 36 and signal interconnects. Signals from different channels are time division multiplexed with a sampling rate sufficiently high to avoid data loss (e.g. sampling rate eight times greater than the sampling rate of an individual channel). Alternatively, the receiver 34 outputs signals for each channel on separate signal lines. In yet another alternative embodiment, the receiver 34 includes analog or digital receive beamforming circuits.

The analog-to-digital converters 36 comprise separate converters for each channel or for each signal path. In one embodiment, eight 8 bit analog-to-digital converters are packaged together on one chip (e.g. one converter for each of eight multiplexed signal streams). In another embodiment, four chips each with sixteen 8 bit converters are provided (e.g. one converter for each of 64 channels). Other groupings, conversion resolutions and numbers of converters may be used. The analog-to-digital converters 36 are spaced from the ultrasound processor 38, such as being in separate semiconductor chips. To reduce the number of signal lines and the inputs on the ultrasound processor 38, the analog-to-digital converters have a high speed serial output for each chip. Alternatively, each converter outputs to a separate signal line.

The ultrasound processor 38 comprises one or more of a digital signal processor, application specified integrated circuit, general processor, analog device, digital device, detector, transmit beamformer, receive beamformer, scan converter, filter, memory, buffer, data bus, analog devices now known or later developed, digital devices now known or later developed, and combinations thereof. Any of the various ultrasound circuitry and associated software described in the patents cited herein may be used. In one embodiment, the ultrasound processor 38 is a single, small geometry (e.g., only digital or with minimal analog circuits) ASIC operable to demultiplex channel information, down convert, receive beamform, control system operation, detect, scan convert and video filter or process the ultrasound data communicated from the transducer 18 or receiver 34. Fewer, different or additional functions may be performed by the ultrasound processor 38. In this embodiment, digital information is received from analog-to-digital converters 36 separate from the ultrasound processor 38, but the converters 36 may alternatively be integrated with the ultrasound processor ASIC. Different functions may be performed by different components, such as performing receive beamforming in the receiver 34 or scan conversion or video processing in the transmitter 24 or multi-use display device 14.

The ultrasound processor 38 controls generation of transmit waveforms (e.g. transmit beamforming), such as by controlling the transmit beamformer 32. In one embodiment, the ultrasound processor 38 generates digital signals representing one or more transmit waveforms (e.g. amplitude and frequency), delay information and amplitude information for use by the transmit beamformer 32. A single transmit frequency band and scan format is used, but programmable scan format and/or frequency selection for transmit and receive operations may be used. In one embodiment, each transmit channel uses a same waveform with focusing delays free of apodization. The ultrasound processor 38 indicates when to begin a scan and the transmit beamformer 32 sequences through a table of relative delays to scan the patient. The ultrasound processor 38 may alternatively provide the delay information to the transmit beamformer 32.

In one embodiment, the ultrasound processor 38 includes one or more summers operable to sum signals from a plurality of elements output by the demultiplexer, receiver 34 or transducer 18. By applying different delays and/or amplification (i.e., apodization) followed by summing, the ultrasound processor 38 implements a receive beamforming function. In one embodiment, a plurality of receive beams (e.g. sixteen) are formed in parallel in response to one transmission, such as providing a plurality of parallel beamforming paths in the ultrasound processor 38. One or more filters for isolating beamformed information at a desired frequency, such as a fundamental transmit or harmonic of the transmit frequency band, may also be provided. Alternatively, filtering at the receive beamformation stage is not provided.

The ultrasound processor 38 detects the received beamformed ultrasound data. In one embodiment, a B-mode detector is implemented to detect intensity or energy, but Doppler, flow, spectral Doppler, contrast agent or other detectors now known or later developed may alternatively or additionally be used. One or more filters, such as an axial and lateral filters, are included as part of the detector. In one embodiment, filters with fixed coefficients are used, but programmable filtering may be provided.

The ultrasound processor 38 scan converts data associated with the radial scan pattern to generate ultrasound image data in a video format (e.g. Cartesian coordinate format). In one embodiment, a single radial scan format with possible changes in depth limits the number of operations for scan converting. Multiple scan formats and associated scan conversions may be used. Video filtering or processing may also be provided.

In more complex embodiments, additional ultrasound functionality is provided, such as including functions and associated hardware from now known or later developed portable or larger ultrasound systems. For example, color flow, three-dimensional processing, selection and use of different transducers with associated scan formats, different filtering, harmonic receiving, or providing different processes for different types of examination or applications, is provided by the ultrasound processor 38 or the ultrasound circuitry 30. In one embodiment, audio Doppler processing is also incorporated and output to one or more speakers or earphones.

The user controls 20 comprise one or more switches, sliders, buttons, sensors, a trackball, a mouse, a joy stick, a scroll wheel, a microphone (e.g. for voice control) and/or other now known or later developed input devices. In one embodiment shown in FIG. 1, the user controls 20 include a power on/off trigger, and a depth up/down rocker switch or buttons. In one example embodiment, the power on/off trigger is automatically in an "off" position and only positioned in the "on" position while held by the user to conserve power. The depth control may be used for other functions, such as increasing or decreasing an overall gain. Where a gain control input is not provided, a set gain or a software gain control function may be provided, such as disclosed in U.S. Pat. Nos. 5,579,768 and 6,398,733, the disclosures of which are incorporated herein by reference. The housing 16 is free of further user controls 20 for simplicity, but additional controls may be provided, such as any of various control functions provided on other portable or larger ultrasound systems. For example, a button for freezing an image may be provided in addition to the power control, or a set of buttons for menu navigation and selection may be provided.

Figure 7:
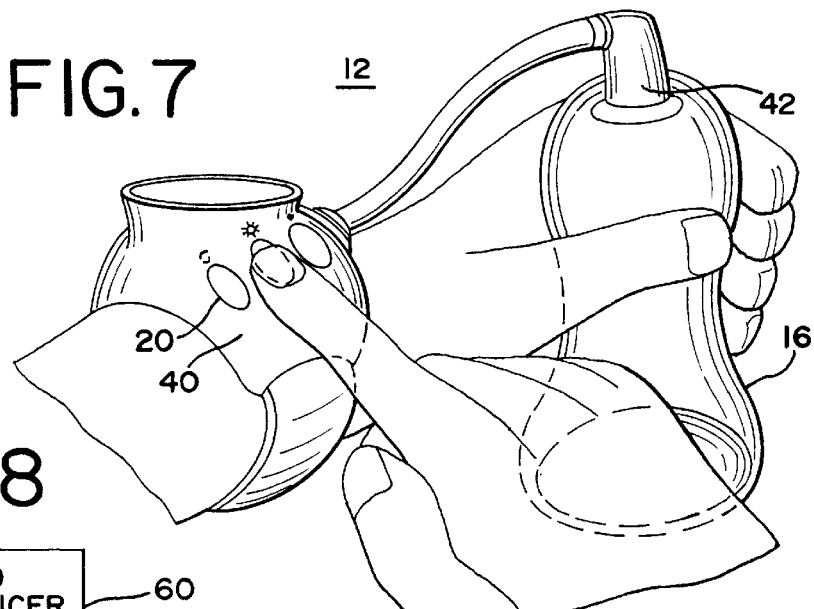

In alternative embodiments, the user controls 20 and/or other components of the ultrasound device 12 are provided in a housing separate from the housing 16. FIGS. 6 and 7 show user input controls 20 in a second housing 40 separate from the first housing 16 and the multi-use display device 14. Through a cord 42 or a signal line, the user input controls 20 communicate with the ultrasound processor 38. Alternatively, the ultrasound processor 38 is positioned in the second housing 40. FIG. 6 shows an embodiment with the second housing 40 configured for placement around a user's wrist. FIG. 7 shows an embodiment with the second housing 40 configured for placement in or over the user's hand. In either embodiment, the first housing 16 includes just the transducer 18, the transducer 18 and some additional ultrasound circuitry (e.g. analog components) or all of the components except for the user controls 20. The second housing 40 includes the remaining components. In alternative embodiments, a wireless connection is provided between the two housings 16, 40. By providing the user controls 20 on the second housing 40, accidental adjustment or changes in the scanning due to movement of the transducer 18 by the user are avoided. In alternative embodiments, use controls 20 are provided on both housings 16, 40.

In yet other alternative embodiments, one or more additional housings are provided for holding one or more components of the ultrasound device 12. For example, a transducer 18 with a separate housing connects with a beamformer and user interface in another housing which connects with a separate housing for the transmitter.

The transmitter 24 comprises a radio frequency, infrared or other now known or later developed transmitter. Multiple transmitters 24 may be provided, such as for line-of-sight based infrared transmitters. In one embodiment, the transmitter comprises a transceiver for bi-directional communication with and control by the multi-use display device 14. The transmitter 24 is operable to wirelessly transmit ultrasound image data in a video format, but other formats, such as data prior to scan conversion, may be used. The transmitter 24 connects to the ultrasound processor 38 within the housing 16, but may be included in a different housing with or without the ultrasound processor 38.

Ultrasound data corresponding to an ultrasound image is encoded, such as MPEG, JPEG or wavelet encoding, and formatted for use with the multi-use display device 14. For example, video data (e.g. NTSC or PAL standard video or computer network image HTML, jpg, or other standard data) is multiplexed using any of various communications formats, such as time or frequency multiplexing, an ultra wide band frequency format or other schemes now known or later developed. The video data corresponds to still or moving (i.e., real time) ultrasound images and includes or is free of control or acquisition time information. The transmission is optimized for any various distances, such as around two meters of range. Multiple directional infrared receivers, directional infrared transmitters and receivers, infrared or radio frequency control or feedback for control of automatic selection of the transmit frequency or receive antennas may be used to reduce the transmit power required. Analog or digital radio frequency transmissions may be used in a low power transmission, such as a digital communication link with 0.1 to 2 megabits per second in an uncompressed or compressed format. In one embodiment, formats for IEEE 802-15A or 11A (Bluetooth) high bandwidth (e.g. 54 Mbytes/sec) standards or other standards now known or later developed are used. In alternative embodiments, the ultrasound data transmitted by the transmitter 24 is free of compression and/or encoding.

The battery 22 comprises a lithium, alkaline or other now known or later developed battery or battery pack. Other various sources of power may be provided for operating the ultrasound device 12 such as a plug or cord may be provided for accessing power from another source. Transmitted power, such as microwaves, may also be provided. As shown in FIG. 1, the battery 22 connects to or within the housing 16 and electrically connects to the ultrasound circuitry. Any of various voltages may be provided by the battery 22, such as 6, 10, 12, 20 or other voltage. In one embodiment, the battery 22 is capable of providing high current for transmitting ultrasound. A voltage divider, transformer or other device may be used to provide two or more different voltages from the battery 22.

FIGS. 2A, 3 and 4 show different embodiments of the multi-use display device 14. The multi-use display device 14 comprises a personal digital assistant (FIG. 2A), a lap top computer (FIG. 3), a tablet computer (FIG. 4), a personal computer, heads-up display, telephone, cellular phone or other display with a processor for use with multiple functions. Using standard video data transmitted from the ultrasound device, the multi-use display device 14 may be an off-the-shelf consumer electronics device, standardized display, or common display device, but proprietary multi-use display devices may be used. The multi-use display device 14 is operable for a use other than associated with ultrasound, such as a calendar, address book, word processing, e-mail or computer network navigation. The multi-use display device 14 is in wireless communication with the ultrasound processor 38. By receiving standard video data corresponding to an ultrasound image, the multi-use display device is also operable to display an ultrasound image responsive to the ultrasound processor 38 as if receiving video data from another non-ultrasound device.

The multi-use display device 14 is separate from the housing 16 or ultrasound device 12. The multi-use display device 14 includes a programmable general processor in a housing 44 with a display 46. In one embodiment, the housing 44 of the multi-use display device 14 is adapted to be portable or handheld, such as being less than 8 inches in any dimension. Larger devices may be used, such as stationary or carted systems. The display 46 comprises a CRT, LCD, plasma screen, a view finder (e.g., electronic displays used on camcorders or other devices to be positioned close to the eye), or other now known or later developed display devices. The display 46 provides any of various resolutions, such as 320×240 pixels, lower or higher resolutions. In one embodiment, the display 46 outputs black and white information, but a color display 46 may be used.

As shown in FIGS. 2A, 3 and 4, the multi-use display device 14 includes a receiver 48 operable to receive the video data. The receiver 48 comprises a receiver or transceiver on a card, in a chip or integrated within the multi-use display device 14. As shown in FIG. 2B, the receiver 48 comprises a card 50 with electrical connectors and an antenna 52. Using firewire, PCMCIA, USB, Bluetooth or other standard connection and communications protocol, the card 50 connects with the multi-use display device 14. For example, the receiver 48 is an off-the-shelf consumer product for connection to an external (shown) or internal port of the multi-use display device 14. The receiver 48 is used for different applications, including receiving non-ultrasound information from devices other than the ultrasound device 12. In an alternative embodiment, the receiver 48 is adapted for ultrasound use, such as including one or more user controls for wirelessly controlling the ultrasound device 12. The receiver 48 includes a memory for storing video data, but a memory included within the multi-use display device 14 may also or alternatively be used. In an alternative embodiment, the receiver 48 is integrated with or is part of the multi-use display device 14 rather than a separable component, such as on a cellular telephone capable of receiving standardized image or picture data.

The receiver 48 receives the data transmitted from the ultrasound device 12 and may transmit control signals to the ultrasound device 12, such as transmit frequency selection, repeat transmission requests, signal format control, and/or ultrasound acquisition control (e.g., start, stop, adjust gain or adjust depth controls). The receiver 48 or processor of the multi-use display device 14 removes any encoding or compression or otherwise detects the standard video data from the transmitted information.

The multi-use display device 14 generates an ultrasound image from the video data. As used herein, video data includes image data such as associated with computer network (e.g. Internet) standards. Common or standard video display software of the multi-use display device 14 automatically or in response to user activation displays the ultrasound images as video data. Any software or other components of a multi-use display device 14 may be used, such as disclosed in U.S. Pat. No. 6,475,146 (Ser. No. 09/962,383), the disclosure of which is incorporated herein by reference. For example, the portable computing device with an integrated video control function using a small, scalable operating system generates the ultrasound images from the video data. As another example, the same portable computing device is used as the multi-use display device 14 for the ultrasound device 12 and to control a larger ultrasound system as disclosed in the above referenced patent.

Alternatively, software adapted for use by the multi-use display device 14 to receive ultrasound data is provided. For example, a computer readable storage medium has data stored therein representing instructions executable by a general processor of the multi-use display device 14. The instructions allow generation of an ultrasound image in response to the ultrasound data. The software instructions interact with the software and hardware of the multi-user display device 14 for decompressing the transmitted video, storing video and displaying images. For example, the date, time and contact information using PIM PDA software is presented with or interleaved with images displayed using the ultrasound software or general use video software.

The ultrasound software may allow for further image processing functions, such as filtering and measurements. For example, the imaging is of a standard depth or size, so each pixel always represents a certain distance and each pixel intensity represents the same acoustic intensity no matter the image. The software includes a calculation package based on the known pixel area or intensity. As another example, the video information includes encoded data representing the scan format, depth, transducer array or other information used for display or measurements. The instructions of the software use the general processor of the multi-use display device 14 to extract the encoded information, but another processor, such as on the card 50, may extract the information. The software may also identify beam drop or missing information and filter, interpolate or ignore to address the missing image information.

The ultrasound software may also allow for control of the ultrasound device 12, such as adjusting a depth, pulse repetition rate, type of imaging, filtering or other scanning or image processing characteristic. Using input devices of the multi-use display device 14, such as a keyboard, mouse, trackball, touch sensitive screen or other now known or later developed input in combination with the software for identifying the input, ultrasound control information is input. The receiver 48 comprising a transceiver communicates the control information to the ultrasound device 12, but other wireless or wired communication links may be used to communicate the control information. For simplicity, control information is not provided from the multi-use display device 14 in one embodiment.

The ultrasound system 10 is adapted for quick and efficient ultrasound scanning in various environments. More than one device may receive the video or other data output by the ultrasound device 12. For example, a heads up display, a video recorder, a hard drive, a CD ROM, a monitor, additional multi-use display devices, a dedicated but remote display device, a computer network, or a memory device receive, display, transmit and/or record the ultrasound images or video formatted data. The ultrasound device 12 may have multiple outputs, such as transmitting at different frequencies for different devices or having a port for corded connection with a display or memory device. An audio output (e.g. speaker) or audio connector may also be provided on the ultrasound device 12 or as part of the multi-use display device 14. Any of the outputs are used in real time with the scan or may be later used where a memory for storing one or more images is provided as part of the ultrasound device 12.

The wireless connection to memory or viewing devices allows for unencumbered scanning while providing ultrasound images to the user and/or others for diagnosis. For example, an ultrasound technician and students each have a multi-use display device 14. The technician scans the patient with the ultrasound device 12 and the ultrasound images are displayed on the various multi-use display devices 14. As another example, a user obtains ultrasound images and stores them on the multi-use display device 14. The user then downloads the images using the multi-use display device 14 to a computer network for sending to another for diagnosis. Using the multi-use display device 14 increases the convenience to the user, and an ultrasound device 12 free of a display reduces the costs of the device.

Figure 8:
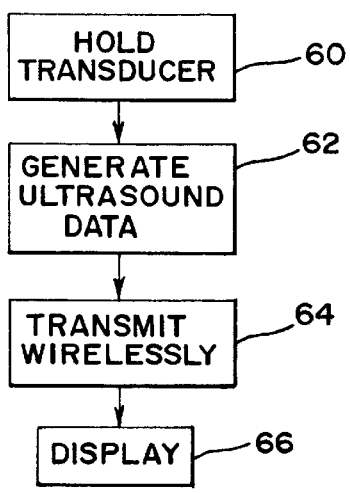
FIG. 8 is a flow chart of one embodiment of a method for using a handheld ultrasound device.

FIG. 8 shows a flow chart of a method for medical diagnostic ultrasound imaging with a handheld system. In act 60, a transducer is held adjacent a patient. For example, the ultrasound device 12 with a transducer 18 in the housing 16 separate from the housing 44 of the multi-use display device 14 is held in a position to scan a patient.

In act 62, ultrasound data representing the patient is generated by the ultrasound device 12. The user activates the ultrasound device 12 by operation of the user controls 20 or a sensor. In response, the ultrasound device 12 transmits and receives acoustic energy. To reduce power requirements for transmission of ultrasound imaging, parallel beamforming where two or more transmit or receive beams are generated simultaneously may be used. Maximum information beam forming may be provided where a plane wave is transmitted and the information received at each receive element is processed in parallel paths or stored in one or more memories for forming a plurality of different receive beams. Phase and amplitude signal processing using reduced power requirements may also be used. By shortening the signal acquisition time, fewer transmit and receive events are used to achieve desired frame rates. Frame rates are the same or less than associated with larger ultrasound systems. While not in use, the analog portions of the transmit and receive circuitry are unpowered or disconnected to save power, such as turning off the analog components about 85% of the time during scanning. Other electronics may be disabled when not in use to conserve power. By limiting the time of actual transmit and receive events relative to the time beamforming and image processing, and temporally interleaving the two, noise is temporally isolated between the transmit and receive functions.

In act 64, the ultrasound data is wirelessly transmitted from the ultrasound device 12 with the portable housing 16 to the multi-use display device 14. The ultrasound device 12 transmits video data, such as standardized image data for use by the multi-use display device 14. Providing the ultrasound image data in a video format allows display by the multi-use display device 14 with no or minimal changes or re-programming. In embodiments where the ultrasound device 12 is free of a display, ultrasound examination may be provided with smaller and/or less expensive equipment since common or already existing displays are used.

In act 66, the ultrasound image is displayed on the multi-use display device 14. A standard video image is displayed based on the video data. The video image includes an ultrasound image. In one embodiment, only the scanned region is displayed. In other embodiments, the ultrasound device 12 or the multi-use display device 14 inserts or adds additional information to the displayed image. For example, the multi-use display device 14 adds annotations, date and time or reference information to the displayed image based on the user's input or a programmed function. As another example, the ultrasound device 12 adds scan depth, time or other information to the video data as part of the image or encoded for extraction and use by the multi-use display device 14.

While the invention has been described above by reference to various embodiments, it should be understood that many changes and modifications can be made without departing from the scope of the invention. For example, any number of handheld or portable components may be used. As another example, any of various ultrasound processes may be implemented. As yet another example, a cord connects the ultrasound device 12 to the multi-use display device 14. A dedicated display may additionally or alternatively be used.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. A handheld system for medical diagnostic ultrasound imaging, the system comprising:
    a transducer;
    an ultrasound processor in communication with the transducer;
    a first housing for the ultrasound processor, the first housing adapted to be handheld; and
    a multi-use display device separate from the first housing and operable to receive wireless communication from the ultrasound processor, the multi-use display device operable for a use other than associated with ultrasound and operable to display an ultrasound image responsive to the ultrasound processor.

2. The handheld system of claim 1 wherein the multi-use display device comprises an off-the-shelf consumer electronics device.

3. The handheld system of claim 1 wherein the multi-use display device comprises a standardized display device selected from the group of: a personal digital assistant (PDA), a laptop computer and a tablet computer.

4. The handheld system of claim 3 wherein the multi-use display device comprises a PDA.

5. The handheld system of claim 1 wherein the multi-use display device comprises a programmable general processor in a second housing, the second housing adapted to be handheld.

6. The handheld system of claim 1 further comprising a probe housing separate from the first housing, the transducer within the probe housing.

7. The handheld system of claim 1 further comprising:
    a multiplexer connected between the transducer and the ultrasound processor; and
    a summer within the first housing, the summer operable to sum signals from a plurality of elements output by the multiplexer.

8. The handheld system of claim 1 wherein the transducer is within the first housing.

9. The handheld system of claim 1 further comprising user input controls in a second housing, the second housing separate from the first housing and the multi-use display device, the user input controls in communication with the ultrasound processor.

10. The handheld system of claim 1 wherein the ultrasound processor comprises an application specific integrated circuit.

11. The handheld system of claim 10 further comprising analog-to-digital converters spaced from the application specific integrated circuit.

12. The handheld system of claim 1 further comprising a transceiver connected to the ultrasound processor within the first housing.

13. The handheld system of claim 1 further comprising a transmitter connected to the ultrasound processor, the ultrasound processor operable to scan convert ultrasound image data, the transmitter operable to transmit video data, and the multi-use display device operable to receive the video data and generate an ultrasound image.

14. The handheld system of claim 1 wherein the first housing is less than 8 inches in any dimension and the multi-use display device is less than 8 inches in any dimension.

15. A method for medical diagnostic ultrasound imaging with a handheld system, the method comprising:
   (a) holding a transducer adjacent a patient;
   (b) generating ultrasound data representing the patient;
   (c) wirelessly transmitting the ultrasound data from a first portable housing to a multi-use display device, the multi-use display device operable for a use other than associated with ultrasound; and
   (d) displaying an ultrasound image on the multi-use display device.

16. The method of claim 15 wherein (c) comprises transmitting the ultrasound data to a programmable general processor in a second housing, the second housing adapted to be handheld.

17. The method of claim 15 wherein (a) comprises holding a probe housing separate from the first portable housing, the transducer within the probe housing.

18. The method of claim 15 further comprising:
   (e) multiplexing data from the transducer; and
   (f) beamforming the multiplexed data.

19. The method of claim 15 further comprising:
   (e) inputting user controls of the system on a second portable housing separate from the first portable housing.

20. The method of claim 15 further comprising:
   (e) converting analog signals from the transducer to digital signals with converters separate from an application specific integrated circuit; and
   (f) image processing the digital signals with the application specific integrated circuit.

21. The method of claim 15 wherein (c) comprises wirelessly transmitting the ultrasound data as video data and wherein (d) comprises displaying a video image from the video data.

22. The method of claim 15 wherein the first portable housing is separate from the transducer.

23. The method of claim 22 wherein the first portable housing is adapted to be worn by the user.

24. A handheld system for medical diagnostic ultrasound imaging, the system comprising:
   a handheld image processing ultrasound device free of a display; and
   a transmitter housed with the handheld image processing ultrasound device, the transmitter operable to wirelessly transmit ultrasound image data in a video format.

25. The handheld system of claim 24 further comprising a computer readable storage medium having data stored therein representing instructions executable by a general processor, the instructions operable to generate an ultrasound image in response to the ultrasound image data.

26. The handheld system of claim 25 wherein the instructions are operable on a multi-use display device separate from the handheld image processing ultrasound device, the multi-use display device operable for a use other than associated with ultrasound.

27. The handheld system of claim 24 wherein the handheld image processing ultrasound device comprises at least one housing, the at least one housing having a scan converter operable to generate the ultrasound image data in the video format.

28. A method for medical diagnostic ultrasound imaging with a handheld system, the method comprising:
   (a) generating ultrasound image data in a video format with a handheld ultrasound device;
   (b) wirelessly transmitting the ultrasound image data in the video format from the handheld ultrasound device.

29. The method of claim 28 wherein the handheld ultrasound device is free of a display, and (b) comprises wirelessly transmitting the ultrasound image data to a multi-use display device separate from the handheld ultrasound device, the multi-use display device operable for a use other than associated with ultrasound.

30. The method of claim 28 further comprising:
   (c) providing a computer readable storage medium having data stored therein representing instructions executable by a general processor, the instructions operable to generate an ultrasound image in response to the ultrasound image data.

* * * * *